United States Patent
Bolm et al.

(12)

(10) Patent No.: US 6,180,551 B1
(45) Date of Patent: Jan. 30, 2001

(54) PROCESS FOR PREPARING MEO-PEG-PROTECTED DIHYDROQUININE OR DIHYDROQUINIDINE DERIVATIVES, NEW DIHYDROQUININE OR DIHYDROQUINIDINE DERIVATIVES AND THEIR USE

(75) Inventors: Carsten Bolm, Aachem; Arne Gerlach, Aachen; Karlheinz Drauz, Freigericht; Andreas Bommarius, Frankfurt, all of (DE)

(73) Assignee: Degussa AG, Hanau (DE)

( * ) Notice: Under 35 U.S.C. 154(b), the term of this patent shall be extended for 0 days.

(21) Appl. No.: 09/504,183

(22) Filed: Feb. 15, 2000

Related U.S. Application Data

(63) Continuation-in-part of application No. 09/308,210, filed as application No. PCT/EP97/06396 on Nov. 17, 1997.

(30) Foreign Application Priority Data

Nov. 20, 1996 (DE) ............................................. 196 47 899

(51) Int. Cl.⁷ ....................... C07D 487/04; C07D 453/04; C08G 65/00
(52) U.S. Cl. ............................................ 502/100; 544/236
(58) Field of Search .............................. 544/236; 502/100

(56) References Cited

PUBLICATIONS

Bolm et al. Asymmetric dihydroxylation with MeO–Polyethyleneglycol–bound ligands. Angew. Chem., Int. Ed. Engl., May 1997.*

* cited by examiner

Primary Examiner—Mukund J. Shah
Assistant Examiner—Hong Liu
(74) Attorney, Agent, or Firm—Omri M. Behr

(57) ABSTRACT

Process for the formation of MeO-Peg-protected dihydroquinine or dihydro quinindine derivatives, new dihydroquinine-or dihyroquinidine derivatives as well as the use thereof. It is known that dihydroquinine or dihydroquinidine derivatives can be successfully used as ligands in the enantioselective dihydroxylation. The new disclosed ligand systems based on dihydroquinine/quinidine, unlike the prior art ligands, can be recycled after enantioselective dihydroxylation by precipitating and filtering the reaction medium, and be reused in the reaction medium. Also disclosed are the ligand systems (I) and (IV), process for preparing the same and their use in the enantioselective dihydroxiation of double bonds.

14 Claims, No Drawings

PROCESS FOR PREPARING MEO-PEG-PROTECTED DIHYDROQUININE OR DIHYDROQUINIDINE DERIVATIVES, NEW DIHYDROQUININE OR DIHYDROQUINIDINE DERIVATIVES AND THEIR USE

RELATED APPLICATIONS

This application is a continuation in part of U.S. Ser. No. 09/308,210 filed Jun. 25, 1999 as a 371 of PCT/EP97/06396 filed Nov. 17, 1997 claiming priority of German Application SN 196 47 889.5 filed Nov. 20, 1996.

FIELD OF THE INVENTION

Process for preparing meo-peg-protected dihydroquinine or dihydroquinidine derivatives

DISCUSSION OF RELATED ART

In *Chem. Rev.* 1994, 94, 2483 (Sharpless, et al), there are described monomeric catalyst systems for enantioselective dihydroxylation based on dihydroquinine and dihydroquinidine derivatives. Although the inantio-selectivity of the charged catalysts is very high, the charged ligands are disadvantageous in the respect that it is difficult or not possible to recycle them and where this is possible, only with poor yield (liquid-liquid extraction yield clearly under 80%).

In *J. Am. Chem. Soc.* 1996, 118, 7632–3 (Janda, et al), there is mentioned the formation of MeO-Peg-protected dihydroquinine, as well as its application in the enantioselective dihydroxylation of double bond containing compounds. The catalyst system mentioned therein achieves the enantioselective dihydroxylation of standard compounds at a level up to 30% worse ee levels as the original system found in Sharpless, et al.

TABLE 1

| Nr. | Olefin Charged | ee-Value Janda et al. | ee-Value Sharpless et al. |
|---|---|---|---|
| 1 | 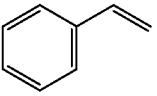 | 88% | 99% |
| 2 | 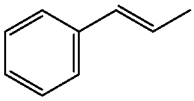 | 60% | 99% |
| 3 | 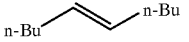 | 85% | 98% |
| 4 | 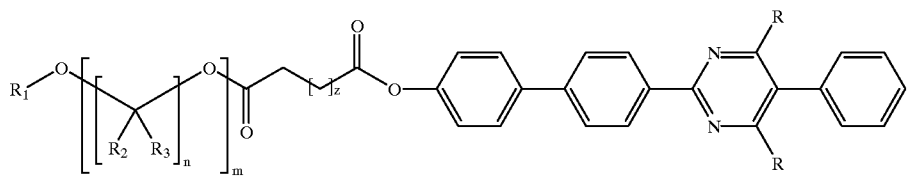 | 43% | 98% |

In Table 1 there are set forth the best enantioselectivities achieved by Janda, et al and Sharpless, et al, in the dihydroxylation of standard compounds with their catalyst or ligand systems. Clearly, the polymer binding of the ligand system under the reaction conditions optimized for a single system, leads to drastically worse ee values.

SUMMARY OF THE INVENTION

The invention refers to new dihydroquinine or dihydroquinidine derivatives of Formulas (I) and (IV), obtainable by the procedures of the present invention, as well as their use for the enantioselective dihydroxylation of double bonds.

The task of the invention was therefore to develop a procedure for the formation of a catalyst system, which gives rise to good ee values such as in the original Sharpless procedure during dihydroxylation and which can be readily separated from the reaction mixture and so becomes available for a new reaction cycle. The task of the invention was further the provision of new catalyst systems that can serve for the asymmetric dihydroxylation of double bonds, as well as the manner and use of their application.

The invention involves a procedure for the manufacture of dihydroquinine derivatives of Formula (I)

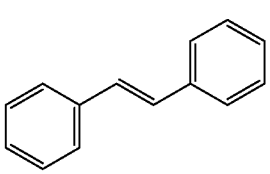

(I)

wherein m is a whole number in the range of 50 to 150, n is a whole number in the range of 1 to 5 and z is a whole number in the range of 0 to 4, $R_1$, $R_2$, and $R_3$ independently of each other are the same or different, $R_2$ and $R_3$ depend upon a variable n, and these have value H, $(C_1-C_5)$-alkyl, being linear or branched, $(C_3-C_8)$-cycloalkyl, aryl, aralkyl, alkylaryl or $(C_1-C_8)$-alkylalkoxy (sic) which may be linear or branched, and R is a residue of Formula (II) or (III)

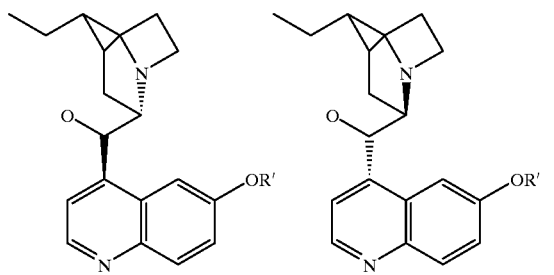

wherein R' is hydrogen, $(C_1-C_5)$ alkyl being linear or branched, $(C_3-C_8)$ cycloalkyl, aryl, aralkyl or alkylaryl, as well as for the formation of dihydroquinidine derivatives of Formula (IV)

(IV)

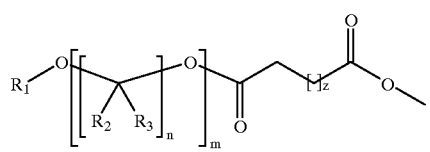

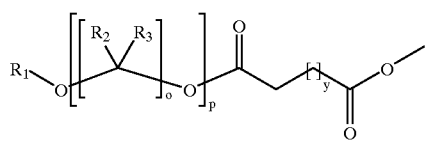

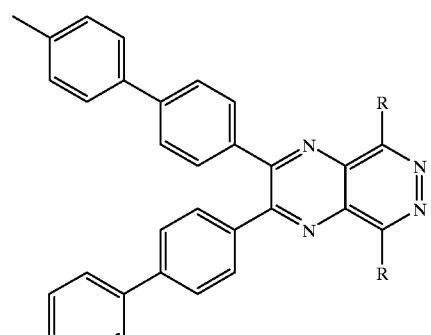

wherein m and p independently of each other are the same or different whole numbers in the range of 50–150, n and o independently of each other are whole numbers in the range of 1–5 and z and y independently of each other are the same or different whole numbers in the range of 0 through 4, and R, $R_1$, $R_2$, and $R_3$ have the same meaning as in Formula (I) wherein $R_2$ and $R_3$ are thereby additionally dependent upon variable o.

When one esterifies compounds of Formula (I) or (VI) with compounds of general Formula (VIII) (see scheme 1), one can obtain compounds of Formulas (II) and (IV) respectively with considerable advantage which can be employed in the enantioselective dihydroxylation with unforeseen success.

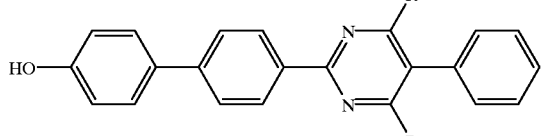

(V)

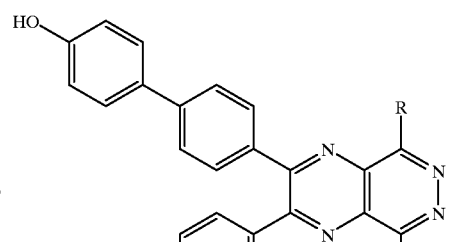

(VI)

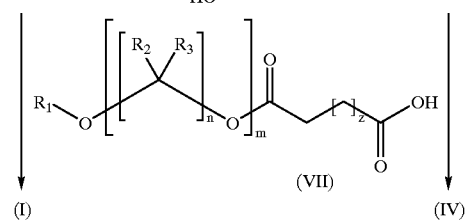

(I)    (VII)    (IV)

The compounds of Formula (V) and (VI) can furthermore be obtained when one reacts compounds of Formulas (VIII) and (IX) with the aromatic compound (X) in the presence of catalytic amounts of a palladium $^{\pm 0}$ compound (see scheme 2) and subsequently removes the silyl protecting group with a fluoride containing agent. It is particularly preferred herein to charge tetrabutyl ammonium fluoride.

with DHQ (II) or DHQD (III).

In a second preferred embodiment, the process of the present invention is characterized thereby that a compound of Formula (IX)

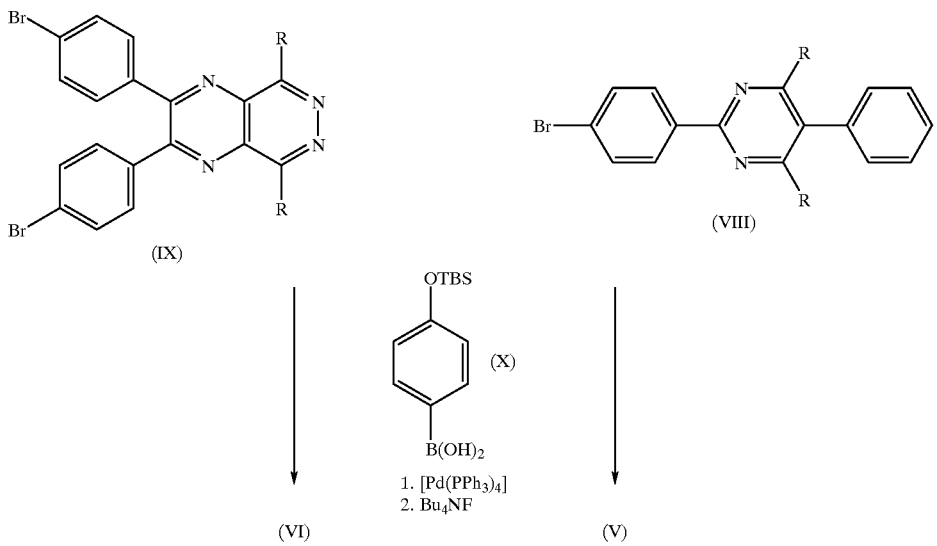

The charged palladium compound comprises advantageously of the elemental metal and a complexing ligand from the series of triphenylphosphine or triphenylphosphite. Particularly preferred is the compound [Pd(PPh$_3$)$_4$].

DESCRIPTION OF THE PREFERRED EMBODIMENTS

The compounds of Formulas (VIII) and (IX) can be obtained in different ways.

In a first preferred embodiment, the procedure is characterized thereby that the compound of Formula (VIII)

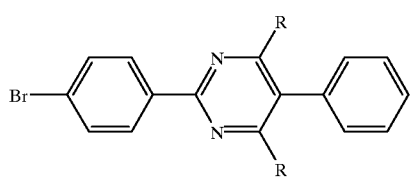

is obtained by reaction of a substance of Formula (XII)

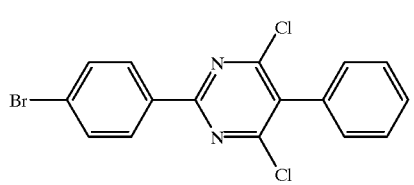

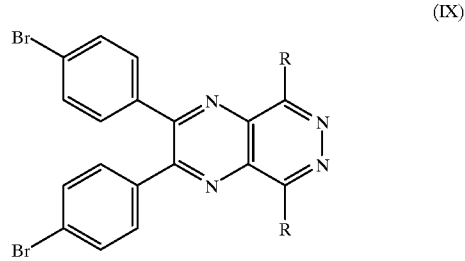

is obtained by reaction of a substance of Formula (XIII)

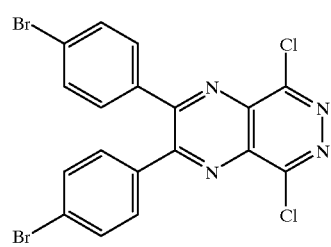

with a DHQ (II) or DHQD (III).

The substances of Formulas (XIII) and (XII) can be prepared in a manner analogous to the procedures known in the literature (*J. Org. Chem.* 1993, 58, 3785), starting from 4-bromo benzonitrile or pyrazine-2,3-dicarboxylic acid in accordance with, for example, *J. Org. Chem.* 1995, 60, 3940.

The new ligand systems of Formulas (I) and (V) are furthermore the subject of the present invention.

The object of the present invention is also the use of the new ligand systems (I) and (IV) which advantageously permit, in the presence of oxidizing agents such as N-methylmorpholine-N-oxide, potassium hexacyanoferrate and/or potassium osmate in a solvent mixture to the dihydroxylation of a double bond in very high enantiomeric excess. A preferred use in accordance with this invention provides that the dihydroxylation is carried out in a solvent mixture containing one or more of the solvents of the group: water, alcohols such as methanol, ethanol, isopropanol, N-propanol, N-butanol, secondary butanol, tert.-butanol, isobutanol, N-pentanol; ethers such as diethylether, tetrahydrofuran, dimethoxy ethane, dioxane; ketones such as acetone, methyl isobutyl ketone, ethyl ketone (sic), diisopropyl ketone; or esters such as acetyl acetic esters or acetic esters, as well as halogenated alkanes such as methylene chloride, chloroform, and trichlorethylene. Preferred solvent mixtures are among others, water tert.butanol, or water acetone. It is particularly advantageous to provide the solvent mixture from at least two of the above-named solvents. Furthermore, the catalysts (I) and (IV) can be readily precipitated after the dihydroxylation by the addition of non-polar organic solvents to the reaction mixture. To the hereto preferred addable solvent materials, there may be counted for example, alkane, such as hexane, cyclohexane, methylcyclohexane; petroleum ethers or ether (sic). Preferred are MTBE, tetrahydrofuran or diethylether as well as DME; ketone, such as acetone, MIBK or ethylmethyl ketone, as well as diisopropyl ketone; esters such as acetic ester or acetyl acetic ester. The temperature of the dihydroxylation lies between −20° C. to +20° C., preferred at temperatures between −10° to +10° C., particularly preferred are temperatures from +2° to −2° C. The recycling occurs as shown in Scheme (III).

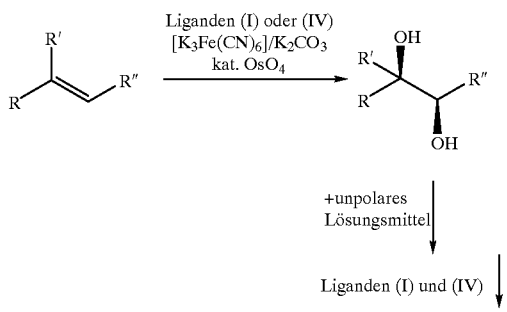

TABLE 2

| R,R',R" | Cat. | % ee* | % ee+ |
| --- | --- | --- | --- |
| Ph,H,Ph | (IV) | 99% | 99% |
| Ph,H,H | (IV) | 98% | 99% |
| Ph,Me,H | (IV) | 95% | 96% |
| $C_8H_{17}$,H,H | (I) | 87% | 89% |
| $Me_3C$,H,H | (I) | 90% | 92% |

*Present Invention
+Sharpless

Table 2 shows the enantioselectivity obtained in the dihydroxylation of standard compounds in accordance with Example 1 in comparison to those obtainable in the catalyst system of Sharpless, et al. The ee values in accordance with the present invention lie minimally lower. After removal of the ligands from the reaction mixture by precipitation with non-polar solvents in over 80% yield, these can be introduced into a new dihydroxylation which is particularly advantageous and quite unexpected.

Table 3 shows the results obtained in a dihydroxylation of styrene, in a manner analogous to Example I in a 6 times sequential introduction of the ligand (IV). The very mild reduction of the ee values is due to loss of alkaloid through minimal ester hydrolysis under the basic conditions of the reaction.

TABLE 3

| | Charged Ligand (IV) | |
| --- | --- | --- |
| Run | Charged Olefin | ee-Value |
| 1 | ![styrene structure] | 98% |
| 2 | " | 98% |
| 3 | " | 98% |
| 4 | " | 98% |
| 5 | " | 97% |
| 6 | " | 96% |

The reaction may optionally be carried out continuously in suitable installation in that one operates with polymer ligands of Formulas (I) of (IV) in a loop reactor and contacts the solution with the compound to be hydroxylated before the dihydroxylation and, after the end of the reaction, separates them by suitable appliances with or without precipitation of the ligands, but with retention of same in the loop reactor.

It is therefore possible to charge the expensive new ligand systems (I) and (IV) for the highly enantioselective dihydroxylation and subsequently to recycle them in a simple manner most advantageously and in very good yields, which contributes to the economically desirable production of enantioselectively enriched 1,2-diols.

The following examples serve to illustrate the invention:

A: Reaction Example

EXAMPLE 1

Dihydroxylation of Styrene

A mixture of 167 mg (15 μmol) $(MeOPEG)_2DPP(DHQD)_2$, 0.99 g (3 mmol) potassium hexacyanoferrate (III), 0.41 g (3 mmol) potassium carbonate and 3.7 mg (10 μmol) potassium osmate in 10 ml t-butanol/water 1:1 were cooled to 0° C. in an ice bath. To this reaction solution, 104 mg (1 mmol) styrene was dripped in under vigorous stirring. After 4 hours, the reaction mixture is treated with 1 g sodium disulfide at 0° C. with care, and allowed to warm to room temperature. The mixture is diluted with 10 ml methylene chloride and separated from the aqueous phase. The ligand is precipitated from the aqueous phase by the slow dripping in of MTBE with vigorous stirring and recovered in good yield (164 mg, 98%). The dihydroxylated styrene remains in the organic solution and can be isolated by concentration and chromatography on silica gel with MTBE in yields of up to 127 mg (92% of theory) and 98% ee.

B: Preparation of the Ligand

EXAMPLE 2

Synthesis from 4-Bromobenzamidene Hydrochloride

To a solution of 0.35 g (15 mmol) of sodium in 150 ml of methanol, there were added 27.30 g (150 mmol) of 4-bromobenzonitrile. Under stirring 48 hours at room temperature 8.0 g (150 mmol) of ammonium chloride were added and stirred for a further 24 hours. The surplus ammonium chloride was filtered off and washed with methanol and methylene chloride (100 ml in each case). After removal of the solvents, there is provided a colorless solid which were subsequently washed with 150 ml diethyl ether. The yield was 11.76 g (50 mmol), 33% theory.

The ether wash solution can be concentrated to yield 16.57 g (91 mmol) of recovered 4-bromobenzonitrile.

$^1$H-NMR (300 MGz, DMSO-d$_6$):☐3.17 (s, 4H; NH), 7.80–7.92 (m, 4H; Ar-H).

Synthesis of 2-(4-bromophenyl)-5-phenyl-4,6-dihydroxypyrimidine

Into a solution of 3.45 g (150 mmol) of sodium in 100 ml methanol, there were sequentially added 10.98 g (47 mmol) 4-Bromobenzamidene hydrochloride and 11.15 g (47 mmol) of phenyl malonic acid ethyl ester. The mixture was heated for 12 hours at 80° C. The deep yellow reaction solution was filtered to remove the precipitated sodium chloride and thereafter the pyrimidine was precipitated with 10 ml of 2 molar hydrochloric acid as an intensive yellow solid. The solid was sequentially washed with water, ethanol and diethyl ether. Yield: 12.70 g (37 mmol, 79% theory) of yellow solid. The pyrimidine is insoluble in all tested organic solvents as well as in water.

m.p. greater >230° C.; High Resolution Mass Spectroscopy (FD): calculated for C$_{16}$H$_{11}$BrN$_2$O$_2$ (M$^+$), 342.0009; Found: 342.0009.

Synthesis of 2-(4-bromophenyl)-5-Phenyl-4,6-dichloropyrimidine

A mixture of 11 g (32 mmol) 2-(4-bromophenyl)-5-phenyl-4,6-dihydroxypyrimidine, 120.6 g (0.79 mmol) phosphoryl chloride and 10.26 g (69 mmol) N,N-diethylaniline was heated for 48 hours at 130° C. The surplus phosphoryl chloride was distilled off and the hot residue freely poured onto a mixture of sodium hydroxide and ice (27 g/270 g) under stirring. Thereafter, extraction was carried out three times with 60 ml diethylether each time. Combined organic phases were sequentially treated with hydrochloric acid, washed neutral with water, dried over magnesium sulfate, filtered and concentrated under reduced pressure. Recrystallization of the residue from acetic ester hexane yields 9.12 g (25 mmol, 75% theory of colorless needless.

m.p.: 133° C. Elemental analysis: C$_{16}$H$_9$Cl$_2$BrN$_2$ (380.07 g/mol); Calc. C 50.56, H 2.39, N 7.37; Found: C 50.54, H. 2.47, N 7.38.

Synthesis of 2-(4-bromophenyl)-4-phenyl-4,6-bis-(dihydroquinidine)-pyrimidine

To 1.62 g (4.26 mmol) 2-(4-bromophenyl)-5-phenyl-4,6-dichloro-pyrimidine and 2.78 g (8.53 mmol) dihydroquinidine in 25 ml toluene, there is added 1.8 g (13 mmol) potassium carbonate and the mixture heated for 2 hours at 130° C. Subsequently, 0.73 g (13 mmol) potassium hydroxide were added and the mixture boiled under a water separator. The toluene is distilled off and the residue taken up in 15 ml of methylene chloride and shaken three times with 10 ml of water each time. The combined organic phases were dried over magnesium sulfate, filtered and concentrated under vacuum. Purification by column chromatography (silica gel, eluent chloroform/ethanol 9:1) yielded 3.06 g (3.2 mmol, 75% theory) of a weakly yellow solid.

m.p. 125–128° C.

Synthesis of 2-(4-Hydroxybiphenyl)-5-phenyl-4,6-bis (dihydroquinidine)-pyrimidine To a solution of 1.44 g (1.5 mmol) 2-(4-bromophenyl)-5-phenyl-4,6,-dichloropyrimidine and 0.132 g (0.11 mmol) of tetrakis(triphenyl-phos-uine) palladium in 15 ml of 2 molar sodium carbonate solution and 45 ml of toluene, there were slowly added 0.75 g (1.88 mmol) of 4-(tert. butyidimethylsilyloxy)-phenyl boric acid in 21 ml of methanol. Subsequently, the mixture was heated under reflux for 24 hours. After cooling, the mixture was diluted with methylene chloride and water with, in each case, 50 mls. The aqueous phase was separated and extracted three times with 10 ml of dichloromethane. The organic phases were combined and dried over magnesium sulfate and concentrated in vacuum. After chromatography on silica gel with MTBE (to remove the surplus boric acid), there was yielded a weakly yellow solid. This was dissolved 35 ml of THF, cooled to 0° C. and slowly treated with 3 ml (3 mmol) of tetrabutyl ammonium fluoride (1 molar in THF). The mixture was then stirred for 15 minutes at 0° C. and for 45 minutes at room temperature. After quenching with 30 ml of water, the THF was removed under vacuum and the residue extracted three times with 10 ml methylene chloride. The combined organic phases were washed with 30 ml of water, dried over magnesium sulfate, filtered and concentrated in vacuo. Cleaning with column chromatography (silica gel; eluent: chloroform/ethanol 9:1) yielded 1.0 g (1.13 mol, 75% of theory) of a weakly yellow solid.

m.p. 178° C.

Synthesis of [2-(4-hydroxybyphenyl)-5-phenyl-4,6-bis (dihydroquinidine)-pyrimidinyl-polyethylene glycol succinate To a mixture of 1.95 g (2 mmol) 2-(hydroxybiphenyl)-5-phenyl-4,6-bis(dihydroquinidine)pyrimidine, 5.10 g (mmol) succinic acid polyethylene glycol ester (mono ester) and 0.024 g (0.2 mmol) 4-dimethylaminopyridine (DMAP), 0.454 g (2.8 mmol) dicyclohexylcarbodiimide (DCC) were added. The mixture was stirred for 12 hours at room temperature. The precipitated dicyclohexyl urea was filtered off. Subsequently, tert butyl methyl ether (MTBE) was added slowly under vigorous stirring and the precipitate was filtered off. The weakly yellow solid was taken up twice in a small amount of methylene chloride and again precipitated with MTBE. The yield is 5.63 g (0.93 mmol), 93% of theory) of a light yellow solid.

m.p.: 56–59° C.

$^1$H-NMR (300 MHz, CDCl$_3$)☐=0.66 (t, J=7.2 Hz; 6 H), 0.92 (m, 4H), 1.19–1.83 (m, 10H), 1.95 (m, 2H), 2.48–3.01 (m, 12H), 3.2–2.9 (Polyethylene glycol peaks), 6.9–7.75 (m, 21H) 8.05 (d, J=9.04 Hz; 2H), 8.79 (m, 2H).

EXAMPLE 3

Synthesis of 23-bis(4-bromophenyl-5,8-dihydroxypyrazino-[2,3-d]-pyridazine

A solution of 7.11 g (50 mmol) 4,5-diamino-3,6-dihydroxy pyridazine and 20 g (54 mmol) 4,4'-dibromobenzyl (sic) (dibromobenzene) in 400 ml of glacial acetic acid were heated for 5 hours at 110° C. (after 10 minutes a yellow precipitate is formed). It was gradually cooled down to room temperature, the precipitate filtered off, and washed twice with 50 ml glacial acetic acid and twice with N-hexane. The yield is 19.03 g (40 mmol, 80% of theory) of a yellow solid.

m.p.:>240° C. Elemental analysis: C$_{18}$H$_{10}$Br$_2$N$_4$O$_2$ (474.11 g/mol); Calc. C 45.60, H 2.13, N 11.82; Found: C 45.81, H 2.29, N 11.85.

Synthesis of 2,3-bis(4-bromphenyl)-5,8-dichlorotriazine-[2,3-d]-pyridazinyl

A mixture of 180 g (38 mmol) 2,3-bis(4-bromophenyl)-5,8-di-ydroxypyrazino-[2,3-d]-pyridazinyl and 15.81 g (756 mmol) phosphorus pentachloride in 200 ml phosphoryl chloride was heated for 90 minutes at 120° C. Subsequently, the phosphoryl chloride was removed in vacuum and the residue taken up in 50 ml ethylene chloride. 6 g of basic aluminum oxide were added and after filtration over silica gel, there is yielded 17.67 g (34 mmol), 91% of theory) of a yellow solid.

m.p. 214–218° C.

Synthesis of 2,3-bis(4-bromophenyl)-5,8-bis-(dihydroquinidine)-pyrazino-[2,3-d]-pyridazinyl To a solution of 0.734 g (2.25 mmol) dihydroquinidine and 0.581 g (5 mmol) N,N,N',N'-tetramethyl ethylene diamine in 16 ml dimethoxy ethane were cooled to −50° C. and slowly reacted with 1.4 mol (2.25 mmol) N-butyl lithium (15% solution in hexane). The red solution was stirred for 15 minutes, permitted to warm to room temperature and treated with 0.511 g (1 mmol) 2,3-Bis(4-bromophenyl )-5,8-dichlorotriazine-[2,3-d]-pyridazinyl solution. Subsequently, it was heated under reflux for 4 hours and diluted with 5 ml water and 25 ml methylene chloride. The mixtures were washed with 20 ml of saturated sodium hydrogen carbonate solution and the aqueous phase extracted three times with 20 ml methylene chloride. The combined organic extracts were dried over magnesium sulfate, filtered and concentrated under reduced pressure. Purification through column chromatography (silica gel; eluent; chloroform-ethanol 9:1 yielded 0.796 g (0.73 mmol) 73% theory.

m.p. 176–180° C.

Synthesis of 5,8-Bis-(Dihydroquinindinyl)2-3, bis-(4-hydroxybiphenyl)-pyrazino-[2,3-d]-pyridazine To a solution of 19.56 g (18 mmol) 2,3-Bis(4-bromiphenyl)-5,8-bis-(dihydroquinindinyl)-pyrazino[2,3-d]-pyridazine and 0.5 g (0.433 mmol) tetrakis-triphenylphosphine)-palladium in 500 ml toluene and 200 ml 2 molar sodium carbonate solution, there was slowly added 13.56 g (54 mmol) of 4-(tert butyl dimethyl silyloxy)-phenyl boric acid in 800 ml methanol. Subsequently, the mixture was heated under reflux for 24 hours. After cooling, a separated aqueous phase was extracted three times with 100 ml methylene chloride and, the combined organic phases dried over magnesium sulfate, filtered and concentrated in vacuum. After column chromatography on silica gel with MTBE (for removal of excess boric acid), there is obtained a yellow solid. This was dissolved in 200 ml THF and slowly treated at 0° C. at 72 ml (72 mmol) with tetrabutyl ammonium fluoride (1 molar in THF). Subsequently the mixture was stirred for 15 minutes at 0° C. and 45 minutes at room temperature. After quenching with 350 ml of water, the THF was removed under vacuum and the residue extracted with 300 ml ethanol/methylene chloride 1:1. The organic phase was washed three times with 100 ml of water, dried over magnesium sulfate, filtered and concentrated in vacuum. Purification through column chromatography (silica gel; eluent, chloroform-ethanol 8:2) yielded 13.68 g (12.2 mmol), 68% of theory) yellow solid.

m.p.: 204–209° C.

Synthesis of [5,8-Bis(dihydroquinindinyl)-2,3-bis-(4-hydroxybiphenyl)-pyrazino-[2,3-d]-pyridazinyl-polyethylene glycol-succinate To a mixture of 1.34 g (1.2 mmol) 5,8-Bis-(dihydroquinindinyl)-2,3-bis(4-hydroxybiphenyl)-pyrazino-[2,3-d}-pyridazine, 13.26 g (2.6 mmol) polyethylene glycol succinate (monoester) and 32 mg (0.26 mmol) DMAP, there was added 2.7 g (13 mmol) of DCC. The mixture was stirred for 48 hours at room temperature and the precipitated dicyclourea was filtered off. MTBE was dripped slowly into the strongly stirred filtrate and thus produced precipitate filtered off. The yellow solid was twice taken up in a small amount of methylene chloride and again precipitated with MTBE. The yield was 12.24 g (1.10 mmol, 92% of theory) of yellow solid. m.p.: 55–58° C.

Synthesis of 4-Bromophenyl-tert.butyldimethylsilyl ether

To a solution of 31.13 g (180 mmol) 4-bromophenol and 32.55 g (216 mmol) tert.butyldimethyl silyl chloride in 600 ml methylene chloride there was added 29.4 g (432 mmol) imidazole. The mixture was stirred for 12 hours at room temperature. After quenching with 1000 ml of water, the aqueous phase was separated and extracted with MTBE (200 ml 3 times). Combined organic phases were washed with saturated sodium chloride solution, dried over magnesium sulfate, filtered off and concentrated in vacuo. Purification through column chromatography (silica gel; eluate MTBE) yielded 50.15 g (17.4 mmol, 97% of theory) of a clear colorless oil.

Elementary analysis: $C_{12}H_{19}BrOSi$ (287.27 g/mol) Calc.: C 50.17 H 6.67; Found: C 50.24 H 6.70.

Synthesis of 4-(tert.Butyldimethyl silyloxyl)-phenyl boric acid

To a suspension of 0.53 g (22 mmol) of magnesium shavings in 200 ml of THF was added 0.5 ml of 5.75 g (20 mmol) (sic) 4-bromophenyl-tert butyl dimethyl silyl ether and a drop of 1,2-dibromo methane. The reaction mixture was briefly heated to reflux to commence the reaction. Subsequently, the rest of the aryl bromide was dripped in slowly. After cessation of the addition, reflux was continued for a further hour. The copper colored solution was cooled to room temperature and added dropwise to a solution of 10.39 g (0.1 mmol) trimethyl borate in 50 ml THF previously cooled to −78° C. The mixture was permitted to rise to room temperature overnight. The mixture was quenched with 30 ml of water and the THF removed under vacuum. The residue was extracted three times with MTBE, the combined organic phases dried over magnesium sulfate, filtered and concentrated in vacuo. Purification by column chromatography (silica gel; eluent MTBE) yielded 4.09 g (16.2 mmol, 81% of theory) of a colorless solid.

$^1$H-NMR (300 MHz, Acetone-$d_6$):□=0.22 (s, 6H; $CH_3$) 0.99 (s, 9H; tBu), 6.86 (m, 2H; Ar-H), 7.79 (s, 2H; Ar-H). Elementary analysis: $C_{12}H_{21}BO_3Si$ (252.19); Calc.: $C_{57.15}$ H 8.39; Found: C 60.16 H 8.44.

What is claimed is:

1. A ligand of Formula (IV)

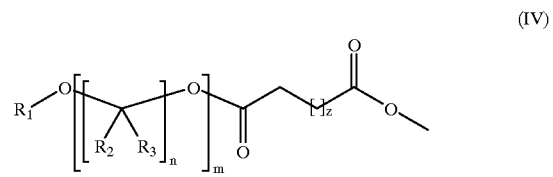

(IV)

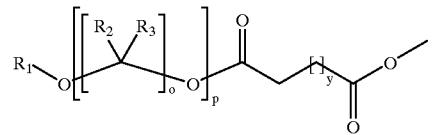

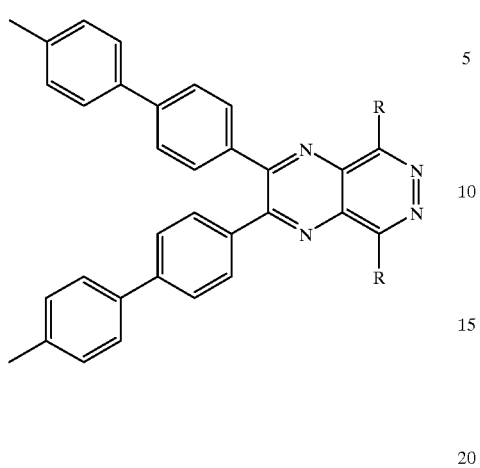

wherein m and p independently of each other may be equal or different integers in the range of 50 to 150, n and o independently of each other are the same or different integers in the range of 1 to 5 and z and y independent of each other are the same or different integers in the range of 0 to 4, and $R_1$, $R_2$ and $R_3$ independently of each other are equal or different, and $R_2$ and $R_3$ depend from n variable, H, $(C_1-C_5)$-alkyl, linear or branched, $(C_3-C_8)$-cycloalkyl, aryl, aralkyl, alklaryl or $(C_1-C_8)$-alkylalkoxy, linear or branched, and wherein $R_2$ and $R_3$ additionally depend from the variable o and R is a residue selected from the group consisting of Formula (II) and (III)

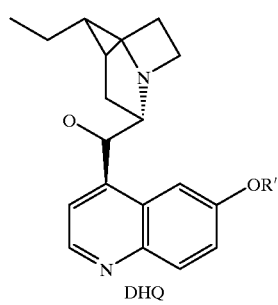

(II)

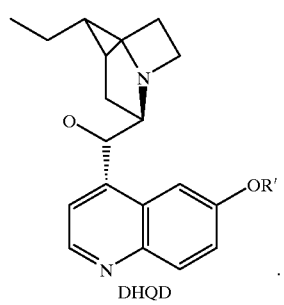

(III)

2. A process for the preparation of a ligand of Formula (IV)

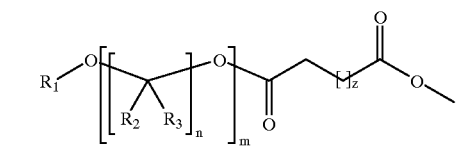

(IV)

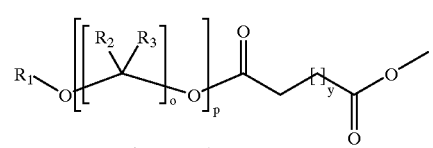

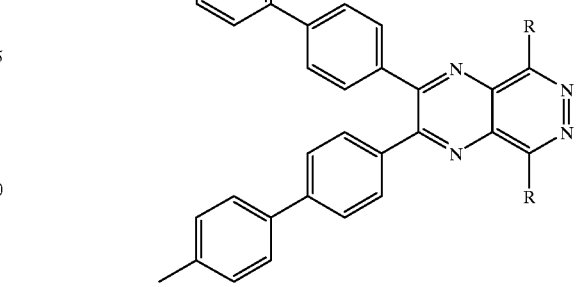

wherein m and p independently of each other may be equal or different integers in the range of 50 to 150, n and o independently of each other are the same or different integers in the range of 1 to 5 and z and y independent of each other are the same or different integers in the range of 0 to 4, and $R_1$, $R_2$ and $R_3$ independently of each other are equal or different, and $R_2$ and $R_3$ depend from n variable, H, $(C_1-C_5)$-alkyl, linear or branched, $(C_3-C_8)$-cycloalkyl, aryl, aralkyl, alklaryl or $(C_1-C_8)$-alkylalkoxy, linear or branched, and wherein $R_2$ and $R_3$ additionally depend from the variable o, which comprises esterifying intermediate products of Formula (VI),

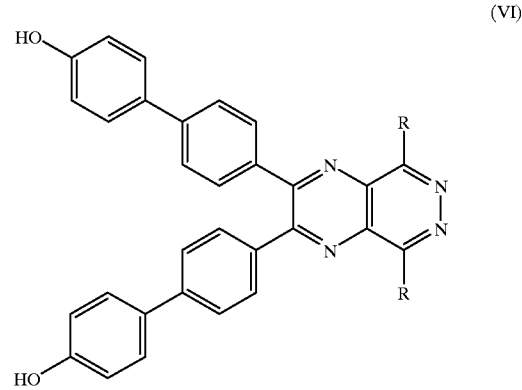

(VI)

and R is a residue selected from the group consisting of Formula (II) and (III)

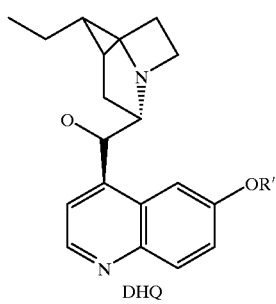

DHQ (II)

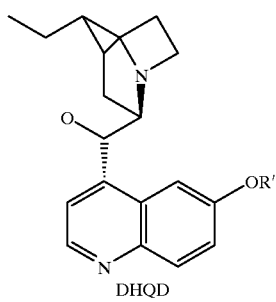

DHQD (III)

wherein R' stands for H, $(C_1-C_5)$-alkyl, linear or branched chain, $(C_3-C_8)$-cycloalkyl, aryl, aralkyl or alkylaryl with a compound of Formula (VII),

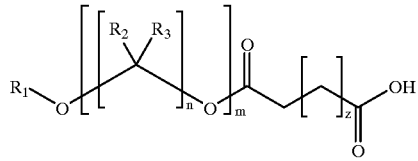

(VII)

wherein m, n and z as well as $R_1$, $R_2$ and $R_3$ have the meanings given for (IV).

3. The process in accordance to claim 2 which comprises producing the intermediate products of Formula (VI) by the reaction of compounds of Formula (IX)

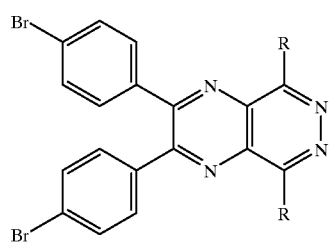

(IX)

wherein R is a residue of Formula (II) or (III) with a compound of Formula (X)

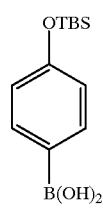

(X)

in the presence of catalytic amounts of palladium and subsequently splitting the silyl group by reaction with a fluoride containing reagent.

4. The process according to claim 2 wherein the catalytically active palladium has the oxidation level ±0 and is complexed with a triphenyl phosphine or triphenyl phosphite ligand.

5. The process according to claim 3, wherein the catalytically active palladium is a compound of Formula (XI)

$$[Pd(PPH_3)_4] \quad (XI).$$

6. The process in accordance with claim 2 wherein the silyl group splitting reagent is a tetraalkyl ammonium fluoride.

7. A process for the catalytic enantioselective dihydroxylation of double bonds in a solvent in the presence of an oxidizing agent wherein the ligands are selected from the group consisting of compounds of Formula (IV)

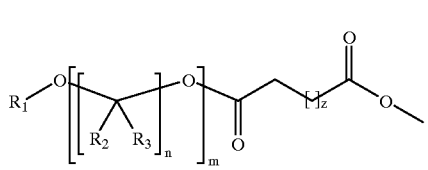

(IV)

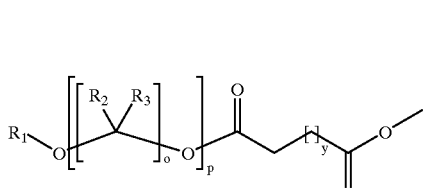

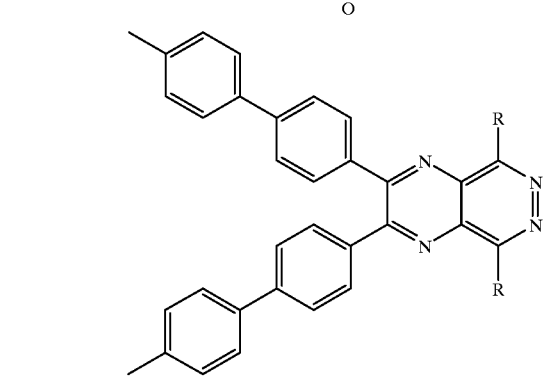

wherein m and p independently of each other may be equal or different integers in the range of 50 to 150, n and o independently of each other are the same or different integers in the range of 1 to 5 and z and y independent of each other are the same or different integers in the range of 0 to 4, and $R_1$, $R_2$ and $R_3$ independently of each other are equal or different, and $R_2$ and $R_3$ depend from n variable, H, $(C_1-C_5)$-alkyl, linear or branched, $(C_3-C_8)$-cycloalkyl, aryl, aralkyl, alklaryl or $(C_1-C_8)$-alkylalkoxy, linear or branched, and wherein $R_2$ and $R_3$ additionally depend from the variable o and R is a residue selected from the group consisting of Formula (II) and (III)

(II)

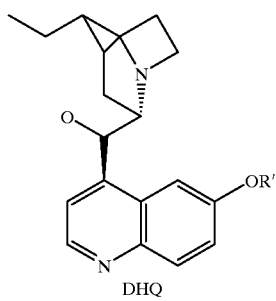
DHQ (III)

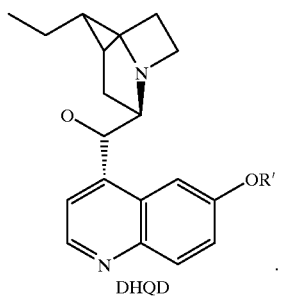
DHQD

8. The process of claim 7 which comprises precipitating the compound of Formula (IV) after the dihydroxylation, and separating them by filtration from the reaction mixture whereby they can again be introduced into the reaction.

9. The process of claim 7 which comprises carrying out the dihydroxylation at a temperature of between −20 and +20° C.

10. The process of claim 7 wherein the solvent is a solvent mixture containing one or more solvents of the group: water, alcohols, ethers, ketones esters and halogenated alkanes.

11. The process of claim 7 wherein the alcohol is methanol, ethanol, isopropanol, n-propanol, n-butanol, secondary butanol, tert. butanol, isobutanol or n-pentanol, the ether is diethyl ether, tetrahydrofuran, dimethoxy ethane or dioxan, the ketone is acetone, methyl isobutyl ketone, ethyl ketone or diisopropyl ketone, the ester is acetyl acetic ester or acetic ester, and the halogenated alkane is methylene chloride, chloroform or trichloroethylene.

12. The process in accordance with claim 7 wherein the oxidizing agent is of potassium hexacyanoferrate or methyl morpholine oxide alone or in the presence of potassium osmate.

13. The process in accordance with claim 12 wherein the oxidizing agent is potassium hexacyanoferrate and potassiium osmate.

14. The process in a ccordance with claim 12 wherein the oxidizing agent is N-methylmorpoline oxide and potassium osmate.

* * * * *